US005938684A

United States Patent [19]

Lynch et al.

[11] Patent Number: 5,938,684

[45] Date of Patent: Aug. 17, 1999

[54] ACCUPRESSURE DEVICE FOR THERAPEUTIC RELIEF

[75] Inventors: Neil T. Lynch, Indian Rocks Beach, Fla.; Neil C. Lynch, Coto de Cuza; Vladimir Dorojinsky, Moorpark, both of Calif.

[73] Assignee: Sierra Self Healing Products, Inc., Agoura, Calif.

[21] Appl. No.: 08/987,334

[22] Filed: Dec. 9, 1997

[51] Int. Cl.$^{6}$ .................................................... A61B 17/00

[52] U.S. Cl. ........................................... 606/204; 606/201

[58] Field of Search .................................... 606/201, 204, 606/204.15, 189

[56] References Cited

U.S. PATENT DOCUMENTS

| | | | |
|---|---|---|---|
| 4,191,178 | 3/1980 | Wisnieski . | |
| 4,233,966 | 11/1980 | Takahashi . | |
| 4,383,342 | 5/1983 | Forster . | |
| 4,421,110 | 12/1983 | DeLisle et al. . | |
| 4,694,831 | 9/1987 | Seltzer . | |
| 5,158,073 | 10/1992 | Bukowski | 606/204 |
| 5,250,067 | 10/1993 | Gelfer et al. | 606/204 |
| 5,312,350 | 5/1994 | Jacobs . | |
| 5,400,526 | 3/1995 | Sessa . | |
| 5,405,311 | 4/1995 | Pecora et al. . | |
| 5,419,758 | 5/1995 | Vijayan . | |
| 5,445,647 | 8/1995 | Choy . | |
| 5,470,304 | 11/1995 | Decanto . | |
| 5,607,749 | 3/1997 | Strumor . | |

*Primary Examiner*—Michael Buiz
*Assistant Examiner*—Vy Q. Bui
*Attorney, Agent, or Firm*—Harris F. Brotman

[57] ABSTRACT

An appliance for therapeutic pressure application, the appliance comprising at least one protuberance each having a base end anchored to a resilient medium and a point end for applying pressure to tissue, the medium having resilient, flexible and insulating properties to absorb in part s the pressure between the point ends and the tissue so as to prevent pain, cut or penetration of the tissue by the point ends and to retain the heat generated by the tissue.

23 Claims, 1 Drawing Sheet

ACCUPRESSURE DEVICE FOR THERAPEUTIC RELIEF

FIELD OF THE INVENTION

The device of the present invention relates to the therapeutic treatment of tissue by means of acupressure. More particularly, this device is a resilient medium studded with rigid protuberances having a base end affixed to the medium and a point end for delivery of acupressure to a tissue or an area.

BACKGROUND OF THE INVENTION

The oriental teachings and healing techniques, including acupuncture and acupressure, have been followed and used for centuries. With the invent of modem medicine, people and medical professionals diverted their attention away from these ancient teachings in favor of chemical compounds. In the recent past, however, the pendulum has swung and the public, including medical professionals, have begun to recognize the values of these ancient teachings.

For obvious reasons, there is reluctance on the part of the public to practice the arts of acupuncture. It requires skill and a novice can do more harm than good. Further, there are significant and obvious issues of sanitation involved in needles that intrude human tissue. Therefore, a less intrusive method of acupressure has been widely favored by the public. It allows for a remedy without intrusion and for some it offers significant relief.

The principal of operation behind acupressure is the delivery of pressure to target tissue, limbs and/or organs. It is believed and in some instances scientifically accepted that the delivery of pressure to specific areas of the human anatomy generates a chemical process beneficial for purposes of pain relief or therapeutic treatment. Moreover, if one can deliver acute multiple pressure points to a given area of the body, the body's normal reaction is to increase the blood flow to that area, thereby stimulating the body's natural system for healing effected or sore tissue.

Although some of the benefits of acupressure have been known, acceptable instruments for delivery of the treatment are not available. In the prior art, the continuum between pressure to the acupressure appliance and pressure to the tissue has been linear because the prior art acupressure appliance directly delivered the pressure applied to it to the tissue. Thus a curve of pressure in to pressure at the tissue has heretofore been substantially linear. The desired end-effect is for an acupressure appliance to deliver the maximum pressure to at least one point of the body or tissue without harming the point at which it applies pressure. For example, a belt studded with fine needles provides for multiple points of acute pressure, however, the needles easily penetrate the skin and therefore are unacceptable acupressure elements.

U.S. Pat. No. 5,250,067 discloses an acupuncture treatment device comprising a flexible pad adapted to be pressed against a person's skin to stimulate blood circulation and safely relieve pain. However, the patented device does not address the shortcoming of applying too much pressure to the needle-like and knife-like protuberances. It is up to the user to monitor the pressure and prevent accidental harm.

Other U.S. Pat. Nos. 5,445,647, 5,607,749, 5,419,758, 5,740,304, 4,191,178, 4,383,342, 4,421,110, 5,158,073, 5,312,350 5,405,311, 4,694,831, 4,233,966 and 5,400,526 describe various means by which one or more pressure points is delivered to a specific area of the body to stimulate therapeutic response. However, no prior art or patent discloses a device that delivers multiple acute pressure points to tissue or area of a body with one or more protuberances in a way that terminates or mitigates the pressure to the tissue or skin short of injury, cutting or intrusion.

SUMMARY OF THE INVENTION

The device of the present invention is an acupressure appliance. It provides for at least one acute pressure point to the subject tissue or area of the body without cutting or penetrating the skin or tissue. It consists of a flexible medium that is resilient under pressure and at least one sufficiently rigid protuberance perpendicularly affixed thereto. The appliance is either applied to the tissue or is placed between the tissue and the floor or bed, allowing the force of gravity upon the user's body to apply pressure to the treated tissue. As the pressure is applied to or through the medium and the protuberances, point ends of the rigid protuberances apply this pressure to the treated area. If too much pressure is applied, the medium, through its resilient properties absorbs the excess pressure so as to not cut or penetrate the skin of the user. Further, the medium is flexible allowing it and the protuberances attached thereto to readily contour to the user's body as he/she lies on it, and/or once lying on it, adjusting one's body to it, and/or allowing it to be wrapped around a limb.

It is therefore the object of this invention to provide for an acupressure appliance delivering mild, moderate or acute pressure points to tissue or any part of the human anatomy via at least one rigid protuberance anchored to a medium having resilient properties, such that excess pressure delivered to the treated area via the point end of the protuberance does not cut or penetrate the tissue. It is further the object of this invention to provide for an acupressure appliance that is sufficiently pliable and flexible to be universally applicable to all parts of the body. It is also a further object of this invention to provide for an acupressure device that is capable of being wrapped about a limb. It is a further object of this invention to provide an acupressure appliance in which the protuberances are substantially perpendicular to the medium and are organized in circular sets of plates independently mounted on said medium and sufficiently spaced apart so as to allow the medium to contour to the treated area and deliver substantially uniform pressure to the treated tissue. It is a further object of this invention to provide for protuberances that have broader base ends affixed to the medium or plates and corresponding point ends for delivery of pressure to the treated tissue, said protuberances having one of any number of cross-sections including, without limitation, a substantially triangular cross-section, a substantially circular cross-section, a substantially rectangular cross-section or substantially trapezoidal cross-section. It is also the object of the present invention to provide for an acupressure appliance that is economical and manufacturable.

DRAWINGS

DETAILED DESCRIPTION OF THE INVENTION

Figures 1, 2, 3, 4, 5, 6:
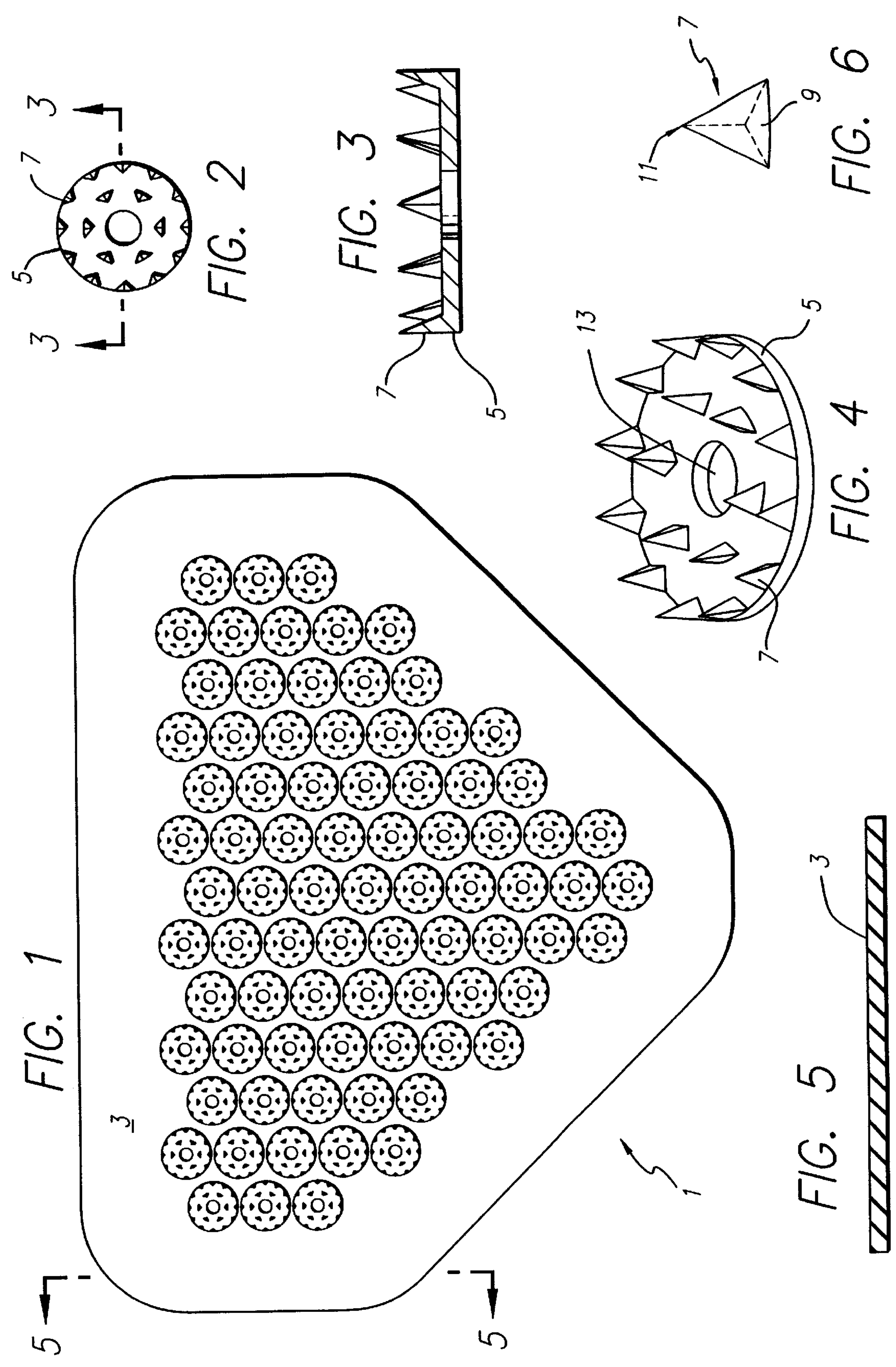
FIG. 1 is a top plan view of the acupressure appliance in accordance with the present invention.
FIG. 2 is a top plan view of a plate having protuberances perpendicularly affixed thereto.
FIG. 3 is a side view of a plate having protuberances perpendicularly affixed thereto.
FIG. 4 is an elevation view of a plate having protuberances perpendicularly affixed thereto.
FIG. 5 is a cutaway view of the medium in accordance with the present invention.
FIG. 6 is an elevation view of an protuberance in accordance with the present invention.

FIGS. 1 through 5 represent the preferred embodiment of the present invention 1. FIG. 1 illustrates device 1 cut in a shape conducive for therapy of the lower back area. Other shapes are equally attainable without deviation from the objects of the present invention. As example, device 1 may comprise a rectangular shape, circular shape, and/or be cut in a form of a belt or a sleeve. As shown in FIG. 5, it consists of a medium 3 having a generally uniform thickness. Medium 3 generally comprises resilient, flexible characteristics. Preferably, medium 3 is made from materials, such as Neoprene®, that are used in the manufacture of wetsuits. It compresses and decompresses to its original shape and thickness and has pressure-absorbing qualities, as well as heat insulating qualities that find utility in the device for preserving heat in the area of the body to which the device is applied. Other materials having similar resilient qualities are equally useable to achieve the objectives of this invention.

As shown in FIG. 1, medium 3 carries a plurality of protuberances 7. In the preferred embodiment, protuberances 7 have a broader base end 9 converging to a point end 11 (see FIG. 6). This provides for structural stability. The cross-section of protuberances 7 can be of any combination, including, without limitation, circular, triangular, rectangular, trapezoidal and the like. They are all equally functional so long as they have a point end 11 at the opposite end of base end 9. The desired cross-sectional diameter dimensions are calculated in part by practical constraints of manufacturing and in part by the number of protuberances 7 the user desires to attach to medium 3 to achieve the desired density of end points 11 for application of therapeutic acupressure to treated tissue.

The height of protuberances 7 may be variable, but preferably uniform to provide uniform pressure through point ends 11 to the tissue. It is understood, however, that if the height is too small, the therapeutic purpose of the device may be diminished as the protuberances 7 are not allowed to apply sufficient pressure to the tissue because the tissue will come to rest on the medium 3 as protuberances 7 are absorbed by the elastic qualities of the skin or tissue. On the other end of the spectrum, it may be economically or practically undesirable to construct protuberances that are very long. As the height dimension of protuberances 7 increases, the moment of pressure at its end points 11 torques its base end 9 and may undesirably deform medium 3 or diminish its resilient properties unproductively. Therefore, in the preferred embodiment protuberances 7 have a height dimension of about $5/32$ of an inch. It is further understood throughout the specification and claims of this invention that the term "tissue" is broadly defined as any mass to which device 1 is applied and includes, without limitation, any part of anatomy such as muscles, limbs, lower back area, back, shoulders and the like.

In the preferred embodiment, protuberances 7 are attached at their base ends 9 to a plate 5. Plate 5 can be a disk in a form of a circle or any other shape. In the preferred embodiment, it is desirable for the protuberances 7 to have uniform height from plate 5 to point ends 11. This delivers uniform pressure to the tissue. Plates 5 are preferably manufactured from plastic, but can be manufactured from any other material so long as they provide for relatively rigid base for base ends 9. Plates 5 are arranged relatively close to each other throughout the surface of medium 3. If too few plates 5 and associated protuberances 7 are arranged about medium 3, the distribution of pressure along the few point ends 11 may cause point ends 11 to penetrate the tissue or cut the skin of the user, which is an undesirable effect. If too many plates 5 and associated protuberances 7 are arranged about medium 3 medium 3 becomes inflexible and its ability to wrap about or contour to the area designated for therapeutic treatment is diminished. Further, plates 5 can be adjacently arranged, as in the preferred embodiment, shown in FIG. 1, or randomly arranged. Means for attaching plates 5 to medium 3 is by use of a cement material, screw, nuts and bolts, or, as in the preferred embodiment by a rivet connecting plate 5 and medium 3 through the opening 13.

The desired density of protuberances 7 and the associated end points 11 is variable. It may be practically undesirable for some applications to have a single protuberance 7 and end point 11, since excess pressure applied through medium 3 may cause point 11 to cause discomfort and/or cut or penetrate the skin or tissue. On the other extreme, the force applied through medium 3 is delivered to the tissue through end points 11 and divided among these points. Therefore, if too many protuberances 7 are affixed to medium 3, the pressure and therapeutic effect at end points 11 is diminished and more pressure or force required.

As shown in FIGS. 2, 3 and 4, in the preferred embodiment protuberances 7 are arranged in groups uniformly affixed to a plate 5 that is shaped in a form of a disk. Plate 5 can also be constructed in the form of a triangle, rectangle, circle, trapezoid or any other geometrical shape. From a practical perspective, plate 5 should be substantially flat and have enough structural integrity to substantially support protuberances 7 thereon without significant deflection of protuberances 7 under pressure applied to or through medium 3. Although plate 5 may be of varying diameter and may support a varying number of protuberances 7, in a universal appliance 1, plates 5 are uniformly sized to about $27/32$ of an inch in diameter, although any diameter may be employed. In the one extreme, a diameter may be to small to support a multiplicity of protuberances 7 having the described base ends 9 and point ends 11. On the other extreme, plate 5 with diameter that is too large diminish the advantage of resilient, flexible characteristics of medium 3 that allow appliance 1 to conform to the tissue or limb of the user and absorb excess pressure to avoid pain, cuts or penetration of the tissue by end points 11.

In the preferred embodiment, protuberances 7 should have a substantially uniform height dimension to uniformly apply pressure to the tissue. Protuberances 7 of varying height may be practically necessary in certain applications and are within the scope of this invention. A combination of shorter and longer protuberances 7 may be desirable to provide supporting characteristics through protuberances 7 in conjunction with supporting, resilient qualities of medium 3. Such shorter protuberances (not shown) may have point ends 11 and/or obtuse ends (not shown).

Protuberances 7 may be arranged on plate 5 in any manner. They can be arranged in a random manner or uniformly. As shown in FIG. 3, in the preferred embodiment, protuberances 7 are arranged about a circular plate 5. They are equally spaced apart in two concentric rings at their base ends 9 about the circular parameter of plate 5. In one embodiment, there are twelve protuberances 7 at the outer ring and six in the inner ring. The center of plate 5 has a void for receipt of a rivet (not shown) to affix plate 5 to medium 3. Medium 3 and plate 5 may also be joined by any other means such as glue, cement, screw, heat bond, nut and bolt arrangement and the like. Rivets were chosen for the preferred embodiment for their practical and economic qualities. As described above, plate 5 and associated, attached protuberances 7 may be arranged about medium 3 in any configuration or density. The driving factors of the same are the applications for which they are employed and the amount of pressure applied through point ends 11. In the preferred embodiment, plates 5 are adjacently placed throughout medium 3 for universal application. There is sufficient room between plate 5 to allow medium 3 to contour or deform about or under the weight of the tissue to which it is applied.

Base ends 9, for practical structural purposes should have a broader area than point ends 11 to maintain the rigid structure of protuberance 7 for delivery of pressure at its point ends 11. If protuberances 7 are constructed from plastic, uniform cross-section between point end 11 and base end 9 may allow protuberance 7 to flex or bend under pressure. If protuberances 7 are made of sufficiently rigid material with the described uniform cross-section, allowances must be made to provide for strong joint between the base end 9 and plate 5, which may be possible, but likely render the device more expensive and less desirable. This can be overcome, as in the preferred embodiment, by providing broader base ends 9 as compared to point ends 11. The cross-section of base end 9 of the preferred embodiment is triangular. Any other cross-sections such as circular, rectangular, trapezoidal, etc., may be employed without deviating from the objects of this invention.

Point ends 11 of the preferred embodiment comprise a relatively small area. They are not needle like because needles easily penetrate skin or tissue under small amount of pressure. On the other hand they do not comprise a large area, since a sufficiently large end point is not capable of delivering the desired therapeutic effect or requires a large amount pressure to deliver the desired therapeutic effect. Therefore, point ends 11, in the preferred embodiment, come to a point, yet they are sufficiently blunt so as to not pierce the human skin accidentally or without application of significant force thereto.

Medium 3, in accordance with the present invention, is made of a resilient substance such as Neoprene® or other insulative, resilient material employed in construction of marine wetsuits. The resilient characteristics of this material allow medium 3 to be flexible and contour to the anatomy of the user, uniformly spreading the applied pressure to the treated tissues via plates 5 and end points 11. Further, resilient medium 3 also acts as an absorber of excess pressure preventing end points 11 from penetrating or cutting the skin of the user. As the pressure is initially applied to the lower back area, as an example, point ends 11 deflect the natural elasticity of the skin and supporting tissue. As the limit of skin and tissue elasticity is approached, the pressure at end points 11 that exceeds the elasticity capability of the tissue and skin is absorbed by medium 3, so as to prevent the undesirable pain, cuts or skin penetration. The thickness of medium 3 may vary with the application, pressure applied through end points 11 and/or the weight of the user. For most universal applications, a single sheet of medium 3 having a thickness dimension of approximately ⅛ of an inch is sufficient, although the thickness may vary considerably as explained above. Medium 3 is preferably an insulating material that preserves heat in the tissue to which appliance 1 is applied for promoting beneficial effects of the device.

Medium 3 is a planar sheet in the preferred embodiment, although it can be shaped in a form of a sleeve or any other shape to fit its particular purpose and application. FIG. 1 illustrates medium 3 cut in a universal shape conducive for therapeutic treatment of a lower back area. Because it is cut in a form of a flat, planar sheet, it is simple to dimension the cut to fit all or a large majority of users. This makes the preferred embodiment of appliance 1 commercially desirable because one size fits all. Means for securing medium 3 can be by custom tailoring, Velcro® strips, snaps, belt, buttons and the like.

Medium 3 allows the user to employ appliance 1 in any environment in any situation. In addition to its portable qualities due to its light weight and ability to be wrapped into a tight cylindrical shape, user may employ appliance 1 in a sitting, prone or supine positions. Moreover, the user is not constrained to active participation with the appliance that may require him or her to apply the correct amount of pressure without causing pain, skin penetration or cuts. Further, the user is not constrained to the application of appliance 1 only on certain surfaces such as mattress or a foam pad to achieve the desired result.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the same way to achieve substantially the same result are within the scope of this invention.

What is claimed is:

1. An appliance for therapeutic pressure application, said appliance comprising a multiplicity of protuberances, all of substantially uniform length, said protuberances having a multiplicity of base ends anchored to a resilient medium and a multiplicity of pointed ends for applying pressure to tissue, said medium having resilient properties to absorb in part the pressure between said pointed ends and said tissue so as to prevent pain, cut or penetration of said tissue by said pointed ends.

2. The device of claim 1 wherein said protuberances are grouped to at least one common plate by affixing said base ends thereto and said plate attached to one side of said medium.

3. The device of claim 2 wherein said plates are chosen from the group of plates having substantially circular, substantially rectangular, substantially triangular and substantially trapezoidal cross-sections.

4. The device of claim 2 further comprising means for joining said plate to said medium.

5. The device of claim 2 further comprising a rivet for joining said plate and said medium.

6. The device of claim 2 further comprising a cement compound means for joining said plate and said medium.

7. The device of claim 2 further comprising a screw means for joining said plate and said medium.

8. The device of claim 1 wherein said protuberances are substantially adjacently placed about said medium.

9. The device of claim 1 wherein said protuberances are randomly placed about said medium.

10. The device of claim 1 wherein said protuberances are sufficiently rigid so as to not substantially deform under the pressure at said pointed ends to said tissue.

11. The device of claim 1 wherein said medium is shaped to contour to the anatomy of said tissue to which it is applied.

12. The device of claim 1 wherein said protuberances are arranged to contour to the anatomy of said tissue to which they are applied.

13. The device of claim 1 wherein said medium and said protuberances affixed thereto are arranged to contour to the anatomy of said tissue to which they are applied.

14. The device of claim 1 wherein said medium is sufficiently resilient to absorb the excess pressure between said tissue and said pointed ends of said protuberances so as to allow said pointed ends to depress said tissue and provide the therapeutic action without penetrating or cutting said tissue.

15. The device of claim 1 wherein said protuberances are chosen from the group of protuberances having substantially circular, substantially rectangular, substantially trapezoidal and substantially triangular cross-sections.

16. The device of claim 1 wherein the elevation of said pointed ends of said protuberances over said tissue plane is substantially uniform.

17. The device of claim 1 wherein said base ends of said protuberances have larger cross-section diameters than said pointed ends.

18. The device of claim 1 wherein said medium is flexible.

19. The device of claim 1 wherein said protuberances are spaced sufficiently apart to allow pressure applied between said medium and said tissue to create pressure points against said tissue at said pointed ends of said protuberances.

20. The device of claim 1 wherein said protuberances are spaced sufficiently apart to allow said medium and said protuberances to contour about said tissue.

21. The device of claim 1 wherein said protuberances are arranged in a substantially perpendicular orientation to said medium.

22. The device of claim 1 wherein said medium further comprises insulative properties for retaining the heat of the treated tissue.

23. An appliance for therapeutic pressure application, said appliance comprising a resilient base and a multiplicity of protuberances, all of substantially uniform length, said protuberances having a multiplicity of base ends and terminating at a multiplicity of pointed ends for applying pressure to tissue, said base having resilient properties to absorb in part the pressure between said pointed ends and said tissue so as to prevent pain, cut or penetration of said tissue by said pointed ends.

* * * * *